United States Patent
Gammie et al.

(10) Patent No.: US 7,479,567 B2
(45) Date of Patent: Jan. 20, 2009

(54) REACTIVE DISTILLATION OF CHLOROSILANES

(75) Inventors: Andrew Bruce Gammie, Florence, KY (US); Christopher Darren Gatti, Hebron, KY (US); Roland Lee Halm, Midland, MI (US); Christopher James Kozenski, Perry Park, KY (US); Dennis Gene Van Koevering, Midland, MI (US)

(73) Assignee: Dow Corning Corporation, Midland, MI (US)

( * ) Notice: Subject to any disclaimer, the term of this patent is extended or adjusted under 35 U.S.C. 154(b) by 19 days.

(21) Appl. No.: 11/883,987

(22) PCT Filed: Mar. 15, 2006

(86) PCT No.: PCT/US2006/009508

§ 371 (c)(1),
(2), (4) Date: Aug. 8, 2007

(87) PCT Pub. No.: WO2006/104702

PCT Pub. Date: Oct. 5, 2006

(65) Prior Publication Data

US 2008/0154055 A1 Jun. 26, 2008

Related U.S. Application Data

(60) Provisional application No. 60/666,139, filed on Mar. 29, 2005, provisional application No. 60/673,213, filed on Apr. 20, 2005.

(51) Int. Cl.
*C07F 7/12* (2006.01)

(52) U.S. Cl. ...................................................... 556/450
(58) Field of Classification Search ....................... None
See application file for complete search history.

(56) References Cited

U.S. PATENT DOCUMENTS

| 2,719,859 | A | 10/1955 | Nitzsche |
| 4,382,145 | A | 5/1983 | Yeboah |
| 4,609,751 | A | 9/1986 | Hajjar |
| 5,075,479 | A | 12/1991 | Bokerman et al. |
| 5,169,970 | A | 12/1992 | Ohkawa |
| 6,225,490 | B1 | 5/2001 | Nakayama et al. |
| 7,208,617 | B2 | 4/2007 | Gammie |

FOREIGN PATENT DOCUMENTS

GB 2112407 7/1983

OTHER PUBLICATIONS

Chemistry and Technology of Silicones, Academic Press, N.Y., (1968), pp. 192-193.

*Primary Examiner*—Samuel A Barts
(74) *Attorney, Agent, or Firm*—Matthew T. Fewkes

(57) ABSTRACT

Chlorosilanes such as dimethyldichlorosilane are hydrolyzed in a first super-azeotropic hydrochloric acid distillation column A to produce cyclosiloxanes, chlorosiloxanes, and hydrogen chloride gas. The cyclosiloxanes and the chlorosiloxanes are washed and separated according to their volatility in a second sub-azeotropic hydrochloric acid distillation column B, to produce a substantially chloride free volatile cyclosiloxane stream and a substantially chloride free non-volatile siloxane stream. The process is substantially chloride efficient.

17 Claims, 1 Drawing Sheet

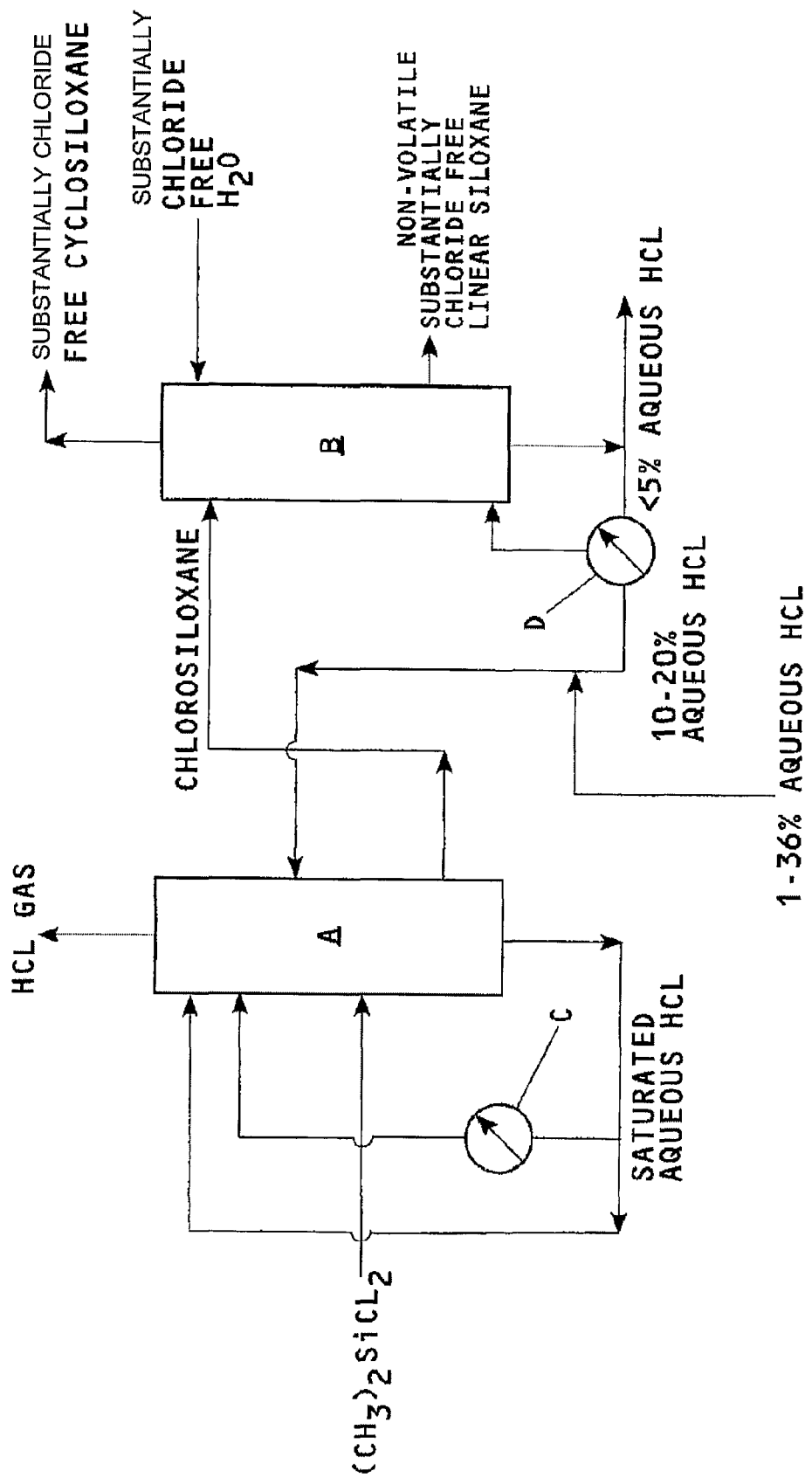

REACTIVE DISTILLATION OF CHLOROSILANES

CROSS REFERENCE TO RELATED APPLICATIONS

This application is a U.S. national stage filing under 35 U.S.C. §371 of PCT application Ser. No. PCT/US2006/009508 filed on 15 Mar. 2006, currently pending, which claims the benefit of U.S. Provisional Patent Application No. U.S. 60/666,139 filed 29 Mar. 2005 and of U.S. Provisional Patent Application No. U.S. 60/673,213 filed Apr. 20, 2005 under 35 U.S.C. §119 (e). PCT application Ser. No. PCT/US2006/009508 and U.S. Provisional Patent Application No. U.S. 60/666,139 and U.S. Provisional Patent Application No. U.S. 60/673,213 are hereby incorporated by reference.

BACKGROUND OF THE INVENTION

This invention relates to a method of minimizing the processing steps normally involved in the recovery of hydrogen chloride in a process of hydrolyzing chlorosilanes to produce a hydrolyzate containing polysiloxanes.

The manufacture of polydimethylsiloxane polymers is a multi-step process. The hydrolysis of chlorosilanes obtained from the direct process is well known in the art and yields a mixture of cyclic and linear silanol-stopped oligomers called hydrolyzate. In some instances, chloro-stopped polymers are also obtained.

The ratio of cyclic to linear oligomers, as well as the chain length of the linear siloxanes, is controlled by the conditions of the hydrolysis, such as the ratio of chlorosilane to water, temperature, contact time, and solvents. Commercially, the hydrolysis of dimethyldichlorosilane is performed by either a batch or a continuous process. In the typical industrial operation, dimethyldichlorosilane is mixed with water in a continuous reactor. The mixture of hydrolyzate and aqueous HCl is separated, preferably by using a simple decanter, which is essentially maintenance-free. However, other means may also be utilized, including variations which combine coalescence technology with gravity separation. Commercially available multistage coalescer separators have been configured using replaceable porous media, to first coalesce and separate the silicone phase from the bulk continuous aqueous phase, and further refine by separating the fine dispersion of aqueous non-continuous phase from the silicone using hydrophobic media. HCl gas containing trace amounts of water is removed, and can be converted to methyl chloride, which can then be reused in the direct process. The hydrolyzate is washed for removal of residual acid, optionally neutralized with base addition or ion exchange technology, dried, and filtered. The typical yield consists of about 35-50 percent of cyclic oligomers, and the remainder consists of linear oligomers. Typically, the cyclic oligomers and the linear oligomers are subsequently separated by distillation. Water can be added to the hydrolyzate, the cyclic oligomers, or the linear oligomers for additional chloride removal.

The complete conversion of dimethyldichlorosilane to only linear oligomers is also possible in the continuous hydrolysis operation. In this operation, the cyclic oligomers are separated from the linear oligomers by a stripping process, and the cyclic oligomers are mixed with the dimethyldichlorosilane. This mixture undergoes equilibration to chloro-terminated oligomers, and is subsequently hydrolyzed. The silanol-stopped linear oligomers are then used in the manufacture of other silicone polymers. Typically, these silanol-stopped linear oligomers are reacted with a suitable endblocking agent such as hexamethyldisiloxane in the presence of a catalyst to obtain low and medium viscosity trimethysiloxy terminated polydimethylsiloxanes.

There is a need in the art for a simplified process that integrates the multi-step process into fewer unit operations. This can be achieved according to this invention by running the process under certain prescribed conditions, feed rates, and inputs into certain equipment for carrying out the processing functions. The simplified process herein provides an economic benefit in reduced capital intensity.

BRIEF SUMMARY OF THE INVENTION

The invention is directed to a method of hydrolyzing chlorosilanes. According to the method, one or more chlorosilanes are fed to a first super-azeotropic hydrochloric acid distillation column, chloride free water is fed to a second sub-azeotropic hydrochloric acid distillation column, HCl gas is removed from the upper portion of the first column, saturated aqueous HCl is removed from the lower portion of the first column and recirculated to the upper portion of the first column, a mixture of cyclosiloxanes and chlorosiloxanes are removed from the first column and fed to the second column, substantially chloride free cyclosiloxanes and non-volatile substantially chloride free siloxanes are removed from the second column, and aqueous HCl is removed from the second column and recirculated to the first column. These and other features of the invention will become apparent from a consideration of the detailed description.

BRIEF DESCRIPTION OF THE DRAWING

The single view of the drawing is a functional representation of the equipment and the general flow pattern of materials used in carrying out the process of the present invention. As can be seen in the drawing, the process equipment includes a first super-azeotropic hydrochloric acid distillation column A, a second sub-azeotropic hydrochloric acid distillation column B, a heat exchanger C for adding heat to the first column A, and a heat exchanger D that vaporizes a portion of the stream containing sub-azeotropic aqueous HCl being recirculated to the first column A as more concentrated liquid sub-azeotropic acid, and to the second column B as a less concentrated vapor stream. The heat exchanger D is equipped to allow flow or portions of flow from the bottom of the second column B to the first column A, back to the second column B, or externally. It should be noted that the first column A contains no inlet for feeding water to the first column A. The water needed for the hydrolysis reaction being carried out in the first column A comes from the sub-azeotropic aqueous HCl stream that is re-circulated from the second column B to the first column A, or it can be provided from an external stream of 1-36 percent aqueous HCl.

DETAILED DESCRIPTION OF THE INVENTION

In a typical chlorosilane hydrolysis process, a chlorosilane such as $R_3SiCl$, $R_2SiCl_2$, and $RHSiCl_2$, where R is as defined below, is reacted with an aqueous phase in a countercurrent mode of operation to form cyclic and linear siloxane products. The chlorosilane injected into the front of the hydrolysis process, is continuously contacted in stages with aqueous phases of decreasing HCl concentration. Reaction water is added to the process at the final stage of reaction/extraction, and is pumped counter-currently through each stage until it is eventually reacted with the feed chlorosilane. Various numbers of stages may be utilized for reaction/extraction to maximize chloride ion recovery and production of siloxanes, with a minimal residual chloride concentration in the final product. Ion exchange technology may be used to reduce the final product chloride concentration to less than 0.2 parts per million (ppm). "Substantially chloride free" as used herein means less than 5 ppm chloride, alternatively less than 1 ppm chloride, alternatively less than 0.5 ppm chloride and alternatively less than 0.2 ppm chloride Additionally, surfactants may be used in the process to affect the percentage of the cyclic and the linear siloxane species present in the final product. Alkaline salt forms of alkyl sulfonates may be used for this purpose, but must first be treated to remove the alkali metal. An ion exchange process may be used for cation removal, and for conversion from the salt form to the alkyl sulfonic acid form of the surfactant.

This invention is directed to a continuous process to hydrolyze chlorosilanes to produce substantially chloride-free volatile cyclosiloxanes and substantially chloride-free nonvolatile linear siloxanes, while recovering chloride as hydrogen chloride gas. The process comprises two countercurrent steps that hydrolyze the chlorosilane to a target molecular weight, separate the volatile and nonvolatile siloxane components at temperatures below their boiling points, while at the same time, separating hydrochloric acid into a stream containing weak or sub-azeotropic aqueous HCl, and hydrogen chloride gas. The first step of the process hydrolyzes the chlorosilanes in super-azeotropic hydrochloric acid, to produce liquid cyclosiloxanes, chlorosiloxanes, and HCl gas. The cyclic fraction and the molecular weight of the siloxanes in the first column A can be controlled by the contact time between the siloxane and aqueous phases, and by the temperature and pressure in the first column. The second step of the process further hydrolyzes and polymerizes the chlorosiloxanes, while separating the volatile and the nonvolatile siloxane streams in the presence of sub-azeotropic hydrochloric acid. Similarly, the cyclic fraction and the molecular weight in the second column B can be controlled by the contact time between the siloxane and aqueous phases, and by the temperature and pressure in the second. In one embodiment the cyclosiloxanes removed from the upper portion of the second column contain more than 95 percent of cyclosiloxanes having less than six silicon atoms. Fresh water is fed to the second step of the process. The sub-azeotropic hydrochloric acid produced in the second step of the process is recycled to the first step of the process. The content of the first column and the second column can be agitated mechanically or as a result of turbulence produced by the vapor/liquid contact within the first column and the second column. The process is also capable of recovering chloride from external sources of, for example, 1-36 percent aqueous HCl as HCl gas.

The chlorosilane feed for the process can contain chlorosilanes of the formula $R_2SiCl_2$. R can be hydrogen or a hydrocarbon radical such as an alkyl group containing 1-20 carbon atoms, a cycloalkyl group, an aryl group, or an aralkyl group. The hydrocarbon radical can be a group such as methyl, ethyl, propyl, isopropyl, n-butyl, isobutyl, tert-butyl, sec-butyl, pentyl, hexyl, phenyl, tolyl, benzyl, and beta-phenylethyl. Some examples of suitable chlorosilanes include compounds such as dimethyldichlorosilane $(CH_3)_2SiCl_2$, diethyldichlorosilane $(C_2H_5)_2SiCl_2$, di-n-propyldichlorosilane $(n-C_3H_7)_2SiCl_2$, di-1-propyldichlorosilane $(i-C_3H_7)_2SiCl_2$, di-n-butyldichlorosilane $(n-C_4H_9)_2SiCl_2$, di-1-butyldichlorosilane $(i-C_4H_9)_2SiCl_2$, di-t-butyldichlorosilane $(t-C_4H_9)_2SiCl_2$, n-butylmethyldichlorosilane $CH_3(n-C_4H_9)SiCl_2$, octadecylmethyldichlorosilane $CH_3(C_{18}H_{37})SiCl_2$, diphenyldichlorosilane $(C_6H_5)_2SiCl_2$, phenylmethyldichlorosilane $CH_3(C_6H_5)SiCl_2$, dicyclohexyldichlorosilane $(C_6H_{11})_2SiCl_2$, and methyldichlorosilane $CH_3SiHCl_2$. The preferred chlorosilanes are dimethyldichlorosilane and methyldichlorosilane $CH_3HSiCl_2$. If desired, chlorosilanes such as $R_3SiCl$ can also be used, where R is the same as defined above. A preferred chlorosilane, for example, is trimethylchlorosilane $(CH_3)_3SiCl$. Mixtures of the above chlorosilanes can also be used. The chlorosilane(s) can be fed to the first column as a liquid or a vapor.

The process of the instant invention uses an essentially stoichiometric amount of water in the hydrolysis, in relation to chloride present on the chlorosilane fed to the process. For purposes of this invention, a stoichiometric equivalence is considered as meaning one mole of water per two moles of chloride added to the process as chlorosilanes. The stoichiometric amount of water is introduced into the process by feeding it to the second sub-azeotropic hydrochloric acid distillation column B. Azeotropic is considered as meaning that the composition is a liquid mixture which retains the same composition in the liquid phase as in the vapor phase as the mixture is distilled at any given pressure.

The processes in columns A and B herein are capable of operation in three modes, namely, a first essentially stoichiometric mode, a second excess of the stoichiometric amount mode, and a third sub or less than the stoichiometric amount mode. In the first stoichiometric mode, all of the water required for both columns A and B is fed to the second column B. No water is fed anywhere else, and no excess of water is fed to the second column B. In this mode, there would be no sub-azeotropic aqueous HCl leaving the stream as shown in the drawing. The aqueous HCl stream at the lower portion of the second column would all be recirculated to the first column A as a liquid and recirculated to the second column B as a vapor.

In the second excess of the stoichiometric amount mode, more water than is required for the two columns A and B is fed to the second column B. In this mode, some water would leave the lower portion of the second column B as a stream of sub-azeotropic aqueous HCL. In the third sub or less than the stoichiometric amount mode, less water than is required for the hydrolysis of the chlorosilanes is fed to the second column B. The water requirement of the first column A is supplied by the acid from the lower portion of the second column B and the feed of external 1-36 percent aqueous HCl.

Water exiting the lower portion of the first column A and recycled is essentially saturated with hydrogen chloride. By essentially saturated is meant that under the process conditions, the water leaving the first column A contains a concentration of hydrogen chloride, such that additional chloride released as a result of the hydrolysis reaction, is evolved from the process as gaseous hydrogen chloride.

The process can be conducted at temperatures ranging from −6° C. to about 150° C. Preferred temperatures are within a range of about −3° C. to 22° C. for the first column A, and within a range of about 100° C. to 110° C. for the second column B. The pressure within the first column A can range from 2-50 psig, while the pressure within the second column B can range from 0-30 psig.

As can be seen in the drawing, the method of hydrolyzing chlorosilanes involves feeding one or more chlorosilanes to the first super-azeotropic hydrochloric acid distillation column A, feeding chloride free water to the second sub-azeotropic hydrochloric acid distillation column B, removing HCl gas from the upper portion of the first column A, removing saturated aqueous HCl from the lower portion of the first column A and recirculating it to the upper portion of the first column A, feeding cyclosiloxanes and chlorosiloxanes from the first column A to the second column B, removing chloride free cyclosiloxanes from the upper portion of the second column B and non-volatile substantially chloride free siloxanes from a lower portion of the second column B, and removing aqueous HCl from the lower portion of the second column B and recirculating it to the first column A. A portion of the saturated aqueous HCl recirculated to the upper portion of the first column A can be heated in the heat exchanger C to provide the energy to vaporize the HCl produced in the chlorosilane hydrolysis reaction. In addition, the aqueous HCl removed from the lower portion of the second column can also be heated and a first portion can be recirculated back into the second column B, while a second heated portion can be recirculated to the first column A. The concentration of the aqueous HCl removed from the lower portion of the second column B can be varied, depending upon the mode of operation of the system as a whole, i.e., stoichiometric mode, excess of stoichiometric mode, and sub or less than stoichiometric mode. The aqueous HCl removed from the lower portion of the second column can be a stream containing less than the azeotropic concentration of aqueous HCl, preferably a stream containing 0-50 percent of the azeotropic concentration of aqueous HCl, and more preferably a stream containing 0-25 percent, alternatively 0.1 to 25 percent, of the azeotropic concentration of aqueous HCl. The water added to column B can be the only source of water added to the system and it can be chloride free. The substantially chloride free water added to column B can be the only water added to column B.

EXAMPLE

The following example is set forth in order to illustrate the invention in more detail.

Example 1

Dimethyldichlorosilane and sub-azeotropic hydrochloric acid was fed to a first super-azeotropic hydrochloric acid distillation column A at mass flow rates of F and 0.17 F respectively. The dimethyldichlorosilane reacted with the water present in the first column A to form cyclosiloxanes, chlorosiloxanes, saturated aqueous hydrochloric acid, and hydrogen chloride gas. The first column A was operated at 10-12 psig and approximately −3° C. to 22° C. The cyclosiloxane/chlorosiloxane product of the first column A was fed at a flow rate of 0.57 F to a second sub-azeotropic hydrochloric acid distillation column B, operated at 0-3 psig and approximately 100-110° C. Fresh chloride free water was fed to the second column B at a rate of 0.14 F. The chlorosiloxane fed to the second column B was washed to substantially chloride free siloxanes by the chloride free water, and the resulting hydrochloric acid was removed from the second column B as a stream containing 5 percent aqueous HCl. The stream containing 5 percent aqueous HCl was heated in a heat exchanger D, and a portion was fed to the first column A at a rate of 0.17 F as 10-20 percent aqueous HCl to hydrolyze the dimethyldichlorosilane. The remaining portion of the 5 percent aqueous HCl was vaporized in heat exchanger D and recirculated to a lower portion of the second column B as <5 percent aqueous HCl vapor. The first column A included a heat exchanger C for adding heat to vaporize the HCl gas exiting the upper portion of the first column A. The washed siloxanes present in the second column B were simultaneously separated into a substantially chloride free cyclosiloxane stream containing >95 percent of $D_3$-$D_5$, i.e., hexamethylcyclotrisiloxane $D_3$, octamethylcyclotetrasiloxane $D_4$, and decamethylcyclopentasiloxane $D_5$, and a substantially chloride-free siloxane stream. The non-volatile stream can be recovered as the end product, or as noted above, it can be further reacted with a suitable endblocking agent such as hexamethyldisiloxane, in the presence of a catalyst, to obtain low and medium viscosity trimethylsiloxy terminated polydimethylsiloxanes.

Other variations may be made in compounds, compositions, and methods described herein without departing from the essential features of the invention. The embodiments of the invention specifically illustrated herein are exemplary only and not intended as limitations on their scope except as defined in the appended claims.

We claim:
1. A method of hydrolyzing chlorosilanes comprising:
 (i) feeding one or more chlorosilanes to a first super-azeotropic hydrochloric acid distillation column, and removing cyclosiloxanes and linear chlorosiloxanes from the first column;
 (ii) feeding substantially chloride free water to a second sub-azeotropic hydrochloric acid distillation column;
 (iii) removing HCl gas from the upper portion of the first column;
 (iv) removing saturated aqueous HCl from the lower portion of the first column and recirculating it to the upper portion of the first column;
 (v) feeding cyclosiloxanes and linear chlorosiloxanes from the first column to the second column;
 (vi) removing substantially chloride free cyclosiloxanes from the upper portion of the second column and non-volatile substantially chloride free siloxanes from a lower portion of the second column; and
 (vii) removing aqueous HCl from the lower portion of the second column and recirculating it to the first column.

2. A method according to claim 1 further comprising:
separating volatile and non-volatile cyclosiloxanes and linear chlorosiloxanes in the second column at temperatures and pressures below their respective boiling points.

3. A method according to claim 2 further comprising:
controlling the molecular weight of the cyclosiloxanes and linear chlorosiloxanes in the first or in the second column as a function of their residence time in the first column or the second column; or as a function of the concentration of HCl in the first column or in the second column.

4. A method according to claim 2 further comprising:
controlling the content of the cyclosiloxanes in the first column or in the second column as a function of their residence time in the first column or in the second column; and as a function of the temperature and pressure in the first column or in the second column.

5. A method according to claim 1 further comprising:
partially vaporizing the aqueous HCl removed from the lower portion of the second column, recirculating a first liquid portion of the heated aqueous HCl to the first column, and recirculating a second vapor portion to a lower portion of the second column.

6. A method according to claim 1 wherein the substantially chloride free water fed to the second column is in an amount ranging from less than the stoichiometric amount required for the amount of chlorosilanes fed to the first column to greater than the stoichiometric amount required for the amount of chlorosilanes fed to the first column.

7. A method according to claim 6 wherein the substantially chloride free water fed to the second column is fed in an amount less than the stoichiometric amount required for the amount of chlorosilanes fed to the first column.

8. A method according to claim 6 wherein the substantially chloride free water fed to the second column is fed in an amount greater than the stoichiometric amount required for the amount of chlorosilanes fed to the first column.

9. A method according to claim 1 further comprising:
feeding 1-36 percent aqueous HCl from an external source to the first column, and recovering the HCl from the external source as HCl gas from the upper portion of the first column.

10. A method according to claim 1 wherein the aqueous HCl removed from the lower portion of the second column is a stream containing less than the azeotropic concentration of aqueous HCl.

11. A method according to claim 10 wherein the aqueous HCl removed from the lower portion of the second column is a stream containing 0-50 percent of the azeotropic concentration of aqueous HCl.

12. A method according to claim 10 wherein the aqueous HCl removed from the lower portion of the second column is a stream containing 0-25 percent of the azeotropic concentration of aqueous HCl.

13. A method according to claim 1 wherein the one or more chlorosilanes fed to the first column are selected from the group consisting of dimethyldichlorosilane, diethyldichlorosilane, di-n-propyldichlorosilane, di-1-propyldichlorosilane, di-n-butyldichlorosilane, di-1-butyldichlorosilane, di-t-butyldichlorosilane, n-butylmethyldichlorosilane, octadecylmethyldichlorosilane, diphenyldichlorosilane, phenylmethyldichlorosilane, dicyclohexyldichlorosilane, methyldichlorosilane, and trimethylchlorosilane.

14. A method according to claim 13 wherein the one or more chlorosilanes fed to the first column are a liquid or a vapor.

15. A method according to claim 14 wherein the one or more chlorosilanes fed to the first column include dimethyldichlorosilane.

16. A method according to claim 1 wherein the substantially chloride free cyclosiloxanes removed from the upper portion of the second column contain more than 95 percent of cyclosiloxanes containing less than six silicon atoms.

17. A method according to claim 1 wherein the content of the first column and the second column is agitated mechanically or as a result of turbulence produced by the vapor/liquid contact within the first column and the second column.

* * * * *